United States Patent
Choi et al.

(10) Patent No.: US 7,446,127 B2
(45) Date of Patent: Nov. 4, 2008

(54) CHROMAN CARBOXYLIC ACID DERIVATIVES FOR THE TREATMENT OF DIABETES AND LIPID DISORDERS

(75) Inventors: Yong Moon Choi, Pine Brook, NJ (US); Hunwoo Shin, Livingston, NJ (US); Palanichamy Ilankumaran, Pinerbrook, NJ (US); Hong Wook Kim, Lincoln Park, NJ (US)

(73) Assignee: SK Holdings Co, Ltd., Seoul (KR)

( * ) Notice: Subject to any disclaimer, the term of this patent is extended or adjusted under 35 U.S.C. 154(b) by 331 days.

(21) Appl. No.: 10/926,615

(22) Filed: Aug. 26, 2004

(65) Prior Publication Data

US 2005/0107371 A1    May 19, 2005

Related U.S. Application Data

(60) Provisional application No. 60/498,121, filed on Aug. 27, 2003.

(51) Int. Cl.
*A01N 43/16* (2006.01)
*C07D 263/30* (2006.01)

(52) U.S. Cl. ..................... 514/458; 548/235

(58) Field of Classification Search ................ 548/235; 514/458

See application file for complete search history.

(56) References Cited

U.S. PATENT DOCUMENTS 5,639,771 A * 6/1997 Obata et al. ................. 514/374

FOREIGN PATENT DOCUMENTS

JP          06-32957        11/1994

WO       WO 01/26656 A2    4/2001

OTHER PUBLICATIONS

Lei Tang, Juanhong Yu, Ying Leng, Ying Feng, Yushe Yang and Ruyun Ji, "Synthesis and Insulin-Sensitizing Activity of a Novel Kind of Benzopyran Derivative", Bioorganic & Medicinal Chemistry Letters 13 (2003) 3437-3440.*

R. J. Jarett, "Type 2 (non-insulin-dependent) diabetes mellitus and coronary heart disease- chicken, egg or neither?", Diabetologia, 1984, 26: 99-102.*

* cited by examiner

*Primary Examiner*—Rebecca L Anderson
*Assistant Examiner*—Robert Havlin

(57) ABSTRACT

There are disclosed derivatives of 3-chromancarboxylic acid represented by formula I

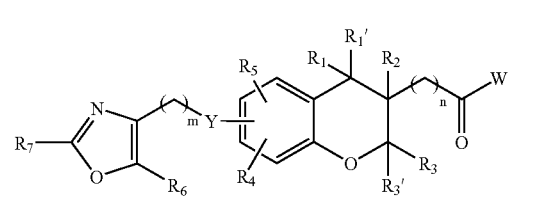

their pharmaceutically acceptable salts thereof and prodrugs thereof which are useful for treatment and control of non-insulin dependent diabetes mellitus (type II diabetes) and its related vascular disease as well as obesity and lipid disorders.

19 Claims, 1 Drawing Sheet

CHROMAN CARBOXYLIC ACID DERIVATIVES FOR THE TREATMENT OF DIABETES AND LIPID DISORDERS

RELATED APPLICATIONS

This application is a continuation of U.S. Provisional Application No. 60/498,121, filed Aug. 27, 2003.

FIELD OF THE INVENTION

The invention is concerned with the 3-chromancarboxylic acid derivatives, their pharmaceutically acceptable salts and prodrugs which are useful for treatment and control of non-insulin dependent diabetes mellitus (type II diabetes) and its related vascular disease as well as obesity and lipid disorders.

BACKGROUND OF THE INVENTION

Diabetes refers to a disease that plasma glucose level is maintained above normal range (>126 mg/dl at fasting status), or hyperglycemia, due to the malfunction of body homeostasis by various reasons. In United States alone, 6.2% of the population (17 million) is suffering from the diabetes which has many complications associated with the macro and micro vascular disease such as coronary heart disease, stroke, hypertension, neuropathy, nephropathy, retinopathy. By American Diabetes Association, adults with diabetes have 2-4 time higher death rate of heart disease and chance of stroke. Each year, 12,000-24,000 people lose their sight and 30,000 people lose their low limb due to diabetes. Control of the blood glucose level significantly decreases the morbidity and complications related with diabetes.

There are two types of diabetes. Type I is a disease which body does not produce insulin due to the destruction of β-cell and type II is a disease which body does not fully utilize insulin due to the increased insulin resistance of the body. Over 90% of the diabetes patients are type II.

Administration of the sulfonylurea drugs such as glyburide and glimepiride stimulate pancreatic β-cell to produce more insulin which compensate the insulin resistance.

Long term use of these insulin secretagogues results in the eventual exhaustion of the β-cell and induction of more resistance at the end. Acute hypoglycemia due to temporal excess of insulin is another adverse effect of these drugs.

Biguanides such as Metformin and Phenformin increase insulin sensitivity to a certain extent but lactic acidosis, nausea and diarrhea are reported as adverse effects.

TZD (thiazolidinedione) type drugs are a more recent addition to the market. They are known to enhance insulin sensitivity by stimulation of PPARγ, peroxisome proliferators activated receptor γ, which is critical for adipocyte differentiation and the modulation of genes involved in energy storage and utilization. TZD drugs are reported to markedly enhance insulin sensitivity and obviate the occurrence of hypoglycaemia but some of it have serious liver toxicity issues and Rezulin was withdrawn from the US market in 2000. Currently, researchers are actively seeking non-TZD based drugs to avoid the liver toxicity potentially associated with thiazolidinedione functional group.

PPARα is reported to be involved in β-oxidation of the fatty acids. Ligands of PPARα such as clofibrate and fenofibrate are known to reduce triglyceride and LDL significantly. As many diabetic patients are accompanied with obesity, dyslipidemia, atherosclerosis and high level of LDLs which worsen the complications, efforts have been made to discover PPARα and PPARγ dual agonist which may correct the abnormalities of blood glucose and dyslipidemia at the same time. Examples are JTT-501 (H. Shinkai et al, *Drugs Future*, 1999, 24), 2-Methyl-2{4-[2-(5-methyl-2-aryloxazol-4-yl)ethoxy]phenoxy}propionic acid (Dawn A. Brooks et al, *J. Med. Chem.*, 2001, 44, 2061-4) and 3-[4-(2-carbazol-9-yl-ethoxy)-phenyl]-2-ethoxy-propionic acid (P. Sauerberg et al, *J. Med. Chem.*, 2001, 44, 2061-4).

The present invention is concerned with the general structure of Formula I, which is a new class of compounds which do not belong to the typical structure of PPARα and PPARγ class, yet effective for lowering blood glucose, insulin and fatty acids. Compounds of general structure of Formula I have potentials as a new class of drugs that has beneficial effects over the current drugs and candidate materials.

SUMMARY OF THE INVENTION

The present invention is concerned with the novel chroman-3-carboxylic acids and its derivatives represented by the Formula I or pharmaceutically acceptable salts and prodrugs thereof;

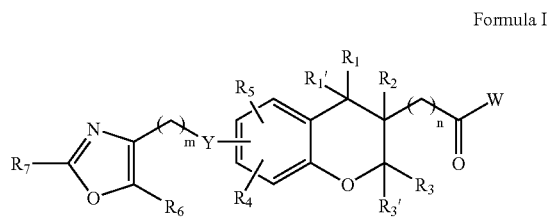

Formula I wherein $R_1$, $R_1'$, $R_2$, $R_3$, $R_3'$, $R_4$, $R_5$, $R_6$, $R_7$, m, n, W, Y and its chiral property are as defined below. Present invention also includes a pharmaceutical composition comprising an effective amount of compounds of Formula I in admixture with a pharmaceutically acceptable carrier or excipient. The present invention is an advance in the art since it provides a new class of pharmaceutically active compounds, which are useful in the treatment, control and prevention of diabetes and its related metabolic diseases.

In biological assay, compounds of Formula I showed marked reduction of glucose, insulin, free fatty acids in db/db and ob/ob mice and thus are expected to exert similar effects in human which may be applicable for the treatment, control and prevention of diabetes, obesity, atherosclerosis, vascular inflammation and their related diseases.

DETAILED DESCRIPTION OF THE INVENTION

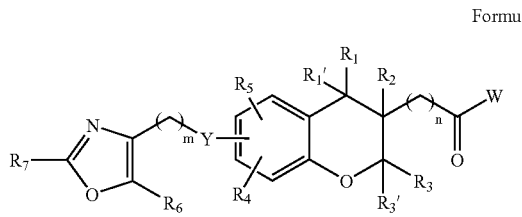

Formula I

Figure 1:
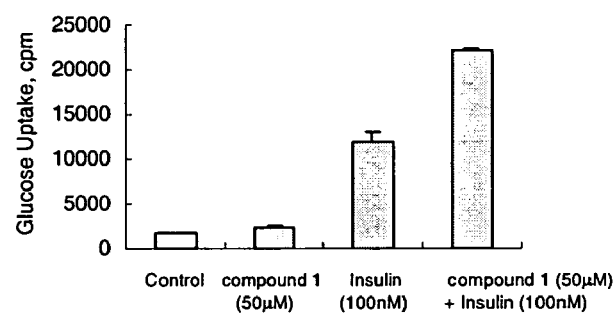
FIG. 1 illustrates an effect of compound of this invention (50 μM) on 2-deoxy-D-glucose uptake in the presence of 100 nM of insulin.

The class of compounds herein does not contain 1,3-thiazolidinedione moiety nor does α-alkoxy/aryloxyacetic acid structures which appears on the various antidiabetic compounds. It showed, however, strong blood glucose lowering effect in ob/ob and db/db mice. They showed good fatty acid lowering effect as well. These compounds have good potential for the treatment and control of diabetes or its related diseases such as hyperglycemia, neuropathy, nephropathy, retinopathy, obesity and also hyperlipidemia or its related diseases like atherosclerosis, inflammatory condition. The present invention includes compounds having the structure of Formula I and its pharmaceutically acceptable salts, admixtures of compounds of Formula I in pharmaceutically acceptable carrier and prodrugs of these compounds.

In the compounds of Formula I, $R_1$, $R_1'$, $R_2$, $R_3$ and $R_3'$ are independently selected from H, $C_{1-7}$ alkyl, $C_{2-7}$ alkenyl, $C_{2-7}$ alkynyl, —Ar, and halogen, wherein alkyl, alkenyl and alkynyl are linear or branched and are optionally substituted with (a) 1-7 halogen atoms and/or (b) 1-3 groups independently selected from (i) —$OC_{1-3}$ alkyl, which is optionally substituted with 1-5 halogen atoms, and (ii) phenyl which is optionally substituted with 1-3 groups independently selected from halogen, $C_{1-5}$ alkyl and —$OC_{1-3}$ alkyl bearing linear or branched and optionally substituted with 1-5 halogen; Ar is selected from the group consisting of aryl, heteroaryl and benzoheterocycle, wherein aryl, heteroaryl and benzoheterocycle are in each instance optionally substituted with 1-5 substituents independently selected from halogen, $C_{1-5}$ alkyl, $C_{2-5}$ alkenyl, $C_{2-5}$ alkynyl, —$OC_{1-5}$ alkyl, —$OC_{2-5}$ alkenyl, —$OC_{2-5}$ alkynyl, —$SO_xC_{1-5}$ alkyl, —$SO_xNR_aR_b$, —$SO_x$phenyl, —$C(O)C_{1-3}$ alkyl and —$C(O)NR_aR_b$ wherein in each case, each alkyl, alkenyl and alkynyl is linear or branched linear or branched and are optionally substituted with (a) 1-7 halogen atoms and/or (b) 1-3 groups independently selected from (i) —$OC_{1-3}$ alkyl, which is optionally substituted with 1-5 halogen atoms, and (ii) phenyl which is optionally substituted with 1-3 groups independently selected from halogen, $C_{1-5}$ alkyl and —$OC_{1-3}$ alkyl bearing linear or branched and optionally substituted with 1-5 halogen; x is selected from 1 or 2, aryl is a carbocyclic 6-10 membered monocyclic or bicyclic aromatic ring system, heteroaryl is a 5- or 6-membered saturated or partly saturated monocyclic heterocycle having 1-4 heteroatoms independently selected from N, S, O in the perimeter of the ring, wherein N may optionally be $NR_a$, and S may optionally be SO or $SO_2$, benzoheterocycle comprises a 5 or 6-membered heterocyclic ring which may be saturated, partially unsaturated or aromatic, and a benzene ring, wherein said heterocyclic ring comprises 1-3 heteroatoms independently selected from O, S, and N in the perimeter of the ring, where N may optionally be $NR_a$ and S may optionally SO or $SO_2$; $R_a$ and $R_b$ are selected from the group consisting of H, $C_{1-5}$ alkyl, $C_{2-5}$ alkenyl, $C_{2-5}$ alkynyl, —$C(O)C_{1-5}$ alkyl, $C(O)C_{2-5}$ alkenyl, —$C(O)C_{2-5}$ alkynyl, $SO_{1-2}C_{1-5}$ alkyl, $SO_{1-2}$phenyl, halogen and phenyl where in all instances, alkyl, alkenyl and alkynyl are linear or branched and are optionally substituted with (a) 1-7 halogen atoms and/or (b) 1-3 groups independently selected from (i) —$OC_{1-3}$ alkyl, which is optionally substituted with 1-5 halogen atoms, and (ii) phenyl which is optionally substituted with 1-3 groups independently selected from halogen, $C_{1-5}$ alkyl and —$OC_{1-3}$ alkyl bearing linear or branched and optionally substituted with 1-5 halogens, wherein halogen is selected from fluorine, chlorine, bromine and iodine;

m and n are independently selected from 0 or the integer of 1-6;

$R_4$ and $R_5$ are independently selected from H, halogen, $C_{1-7}$ alkyl, $C_{2-7}$ alkenyl, $C_{2-7}$ alkynyl, —OH, —$OC_{1-5}$ alkyl, —$OC_{2-5}$ alkenyl, —$OC_{2-5}$ alkynyl, —$C(O)C_{1-5}$ alkyl, —$C(O)C_{2-5}$ alkenyl, —$C(O)C_{2-5}$ alkynyl, —$C(O)OC_{1-5}$ alkyl, —$C(O)OC_{2-5}$ alkenyl, —$C(O)OC_{2-5}$ alkynyl, Ar, —OAr, —$C(O)Ar$, —$C_{3-8}$ cycloalkyl, —$OC_{3-8}$ cycloalkyl, $SO_xC_{1-5}$alkyl, —$SO_xNR_aR_b$, —$SO_xAr$ and —$CONR_aR_b$, where in each case, each alkyl, alkenyl, and alkynyl is linear or branched and is optionally substituted with (a) 1-5 halogen atoms and/or (b) 1-2 groups independently selected from —$OC_{1-3}$ alkyl groups which are linear or branched and are optionally substituted with 1-5 halogens;

Y is selected from —O, —$CR_aR_b$, —$NR_a$, —SO, and —$SO_2$ wherein $R_a$ and $R_b$ are independently selected from the group consisting of H, $C_{1-5}$ alkyl, $C_{2-5}$ alkenyl, $C_{2-5}$ alkynyl, —$C(O)C_{1-5}$ alkyl, —$C(O)C_{2-5}$ alkenyl, —$C(O)C_{2-5}$ alkynyl, $SO_{1-2}C_{1-5}$ alkyl, $SO_{1-2}$ phenyl, halogen and phenyl where in all instances, alkyl, alkenyl and alkynyl are linear or branched and are optionally substituted with (a) 1-7 halogen atoms and/or (b) 1-3 groups independently selected from (i) —$OC_{1-3}$ alkyl, which is optionally substituted with 1-5 halogen atoms, and (ii) phenyl which is optionally substituted with 1-3 groups independently selected from halogen, $C_{1-5}$ alkyl and —$OC_{1-3}$ alkyl bearing linear or branched and optionally substituted with 1-5 halogens;

$R_6$ and $R_7$ are independently selected from H, $C_{1-7}$ alkyl, $C_{2-7}$ alkenyl, $C_{2-7}$ alkynyl and Ar where in each case, alkyl, alkenyl, and alkynyl are linear or branched and are optionally substituted with (a) 1-5 halogen atoms and/or (b) 1-2 groups independently selected from —$OC_{1-3}$ alkyl groups which are linear or branched and are optionally substituted with 1-5 halogens, and Ar is selected from the group consisting of aryl, heteroaryl and benzoheterocycle, wherein aryl, heteroaryl and benzoheterocycle are in each instance optionally substituted with 1-5 substituents independently selected from halogen, $C_{1-5}$ alkyl, $C_{2-5}$ alkenyl, $C_{2-5}$ alkynyl, —$OC_{1-5}$ alkyl, —$OC_{2-5}$ alkenyl, —$OC_{2-5}$ alkynyl, —$SO_xC_{1-5}$ alkyl, —$SO_xNR_aR_b$, phenyl, —$SR_x$ phenyl, —$C(O)C_{1-3}$ alkyl and —$C(O)NR_aR_b$ wherein in each case, alkyl, alkenyl and alkynyl are linear or branched linear or branched and are optionally substituted with (a) 1-7 halogen atoms and/or (b) 1-3 groups independently selected from (i) —$OC_{1-3}$ alkyl, which is optionally substituted with 1-5 halogen atoms, and (ii) phenyl which is optionally substituted with 1-3 groups independently selected from halogen, $C_{1-5}$ alkyl and —$OC_{1-3}$ alkyl bearing linear or branched and optionally substituted with 1-5 halogens, $R_a$ and $R_b$ are as above, and X is selected from an integer of 1-2; and W is selected from the group of consisting of —$OR_a$, —$NR_aR_b$, —$NR_aSO_2R_b$ wherein $R_a$ and $R_b$ are independently selected from the group consisting of H, $C_{1-4}$ alkyl and aryl where in all instances, alkyl is linear or branched and are optionally substituted with (a) 1-7 halogen atoms and/or (b) 1-3 groups independently selected from (i) —OC$_{1-3}$ alkyl, which is optionally substituted with 1-5 halogen atoms, and (ii) phenyl which is optionally substituted with 1-3 groups independently selected from halogen, C$_{1-5}$ alkyl and —OC$_{1-3}$ alkyl bearing linear or branched and optionally substituted with 1-5 halogen.

The compound of C$_3$ configuration according to the present invention comprises (S), (R) or (S)/(R) mixture. Preferably, $R_1$, $R_1'$, $R_2$, $R_3$, $R_3'$, $R_4$ and $R_5$ are independently selected from the group consisting of H, Cl, Br, F, —OC$_{1-4}$ and C$_{1-4}$ alkyl, where said alkyl is linear or branched and is optionally substituted with 1-3 halogens. More preferably, $R_1$, $R_1'$, $R_2$, $R_3$, $R_3'$, $R_4$ and $R_5$ are all hydrogens.

Set forth below are definitions of the radicals covered by Formula I.

The term "alkyl" means a straight or branched hydrocarbon having from 1-7 carbon atoms and includes, for example, methyl, ethyl, n-propyl, n-butyl, sec-butyl, iso-butyl, tert-butyl, n-pentyl, n-hexyl, and the like except where specifically stated otherwise.

The term "halogen" includes fluorine, chlorine, bromine and iodine; the more preferred halogens are fluorine and chlorine.

The term "alkenyl" means carbon chains which contain at least one carbon-carbon double bond, and which may be linear or branched or combinations thereof. Examples of alkenyl include vinyl, allyl, isoprenyl, butenyl, pentenyl, hexenyl, heptenyl and the like.

The term "alkynyl" means carbon chains which contain one carbon-carbon triple bond, and which may be linear or branched or combinations thereof. Examples of alkynyl include acetylenyl, allyl, propagyl, 3-methly-1-pentynyl and the like.

The term "aryl" means mono- or bicyclic aromatic rings containing only carbon rings. Aryl groups that have substituents herein are 6-10 membered monocyclic or bicyclic ring system. Examples of aryl include phenyl and naphthyl, as well as indanyl, indenyl, and tetrahydronaphthyl. Phenyl is most preferred. The term also may describe an aryl group fused to a monocyclic cycloalkyl or monocyclic heterocyclic group.

The term "heterocyclic" means a fully or partially saturated monocyclic or polycyclic ring system containing at least one heteroatom selected from N, S and O, each of said rings having from 3 to 10 atoms, except where defined otherwise. Examples of aryl fused to heterocyclic groups include 2,3-dihydrobenzofuranyl, dihydrobenzopyranyl, and the like. Examples of heterocycles include tetrahydrofuran, piperazine, tetrahydropyran and morphine.

The term "heteroaryl" means a mono-, bi-, or tricyclic aromatic ring containing 1-4 ring heteroatoms selected form N, O, and S (including SO and SO$_2$) in the perimeter of the ring, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, trazinyl, thienyl, pyrimidyl, pyridazanyl, pyrazinyl, benzisioxazolyl, benzoxazylyl, benzothiazolyl, benzimidazolyl, benzofuranyl, benzothiophenyl, quinolyl, indolyl, isoquinolyl, dibenzofuan and the like.

The term "composition" is intended to encompass a product comprising the active ingredient (s), and the inert ingredient(s) that make up the carrier, as well as any product which result directly or indirectly, from combination, complexation or aggregation of any two or more of the ingredients, or from the dissociation of one or more of the ingredients, or from other types of reactions or interactions of one or more of the ingredients. Accordingly, the composition of the present invention encompasses any composition made by admixing a compound of the present invention and a pharmaceutically acceptable carrier.

The term "pharmaceutically acceptable salts" refers to salts prepared from pharmaceutically acceptable non-toxic bases or acids including inorganic or organic bases or organic bases and inorganic or organic acids. Salts derived from inorganic bases include aluminum, ammonium, calcium, copper, ferric, lithium, magnesium, manganese, potassium, sodium, zinc and the like. Particularly preferred are the ammonium, calcium, magnesium, potassium and sodium salts. Salts derived from pharmaceutically acceptable organic non-toxic bases include salts of primary, secondly, tertiary amines, substituted amines including naturally occurring substituted amines such as arginine, betaine, caffeine, choline and the like. When the compound of the present invention is basic, salts may be prepared form pharmaceutically acceptable non-toxic acids, including inorganic and organic acids. Such acids includes acetic, benzensulfonic, enzoic, camphorsulfonic, citric, fumaric, gluconic, glutamic, hydrochloric, hydrobromic, lactic, maleic, malic, mandelic, methansulfonic, mucic, nitric, pamoic, phosphoric, succinic, sulfuric, tartaric, p-toluenesulfonic and the like. Particularly preferred are citric, hydrobromic, hydrochloric, maleic, phosphoric, sulfuric and tartaric acids.

It will be understood that, as used herein, references to the compounds of Formula I are meant to also include the pharmaceutically acceptable salts.

Synthetic Methods

In one embodiment, the compound of this invention can be prepared as follows:

The chroman-3-carboxylic acid moiety is synthesized starting from 2-hydroxy-4-benzyloxybenzaldehyde as described in Scheme 1.

Scheme 1

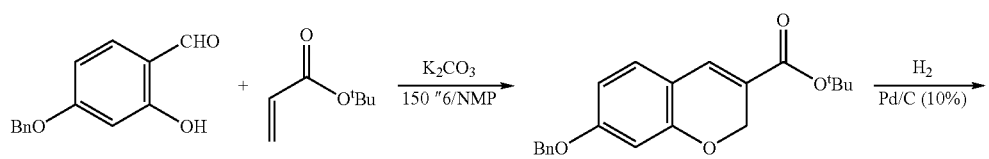

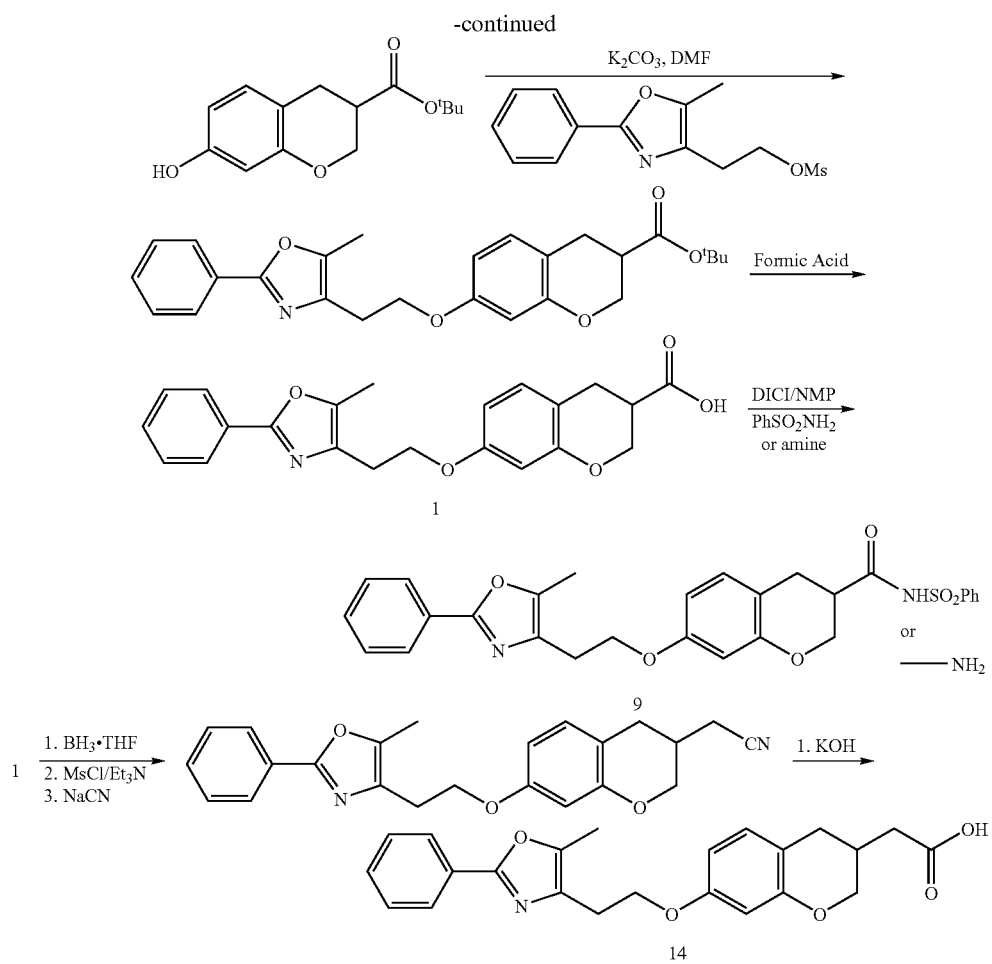

The cyclization is accomplished in NMP at 155° C. in the presence of potassium carbonate and subsequent hydrogenation provides t-butyl 7-hydroxy-chroman-3-carboxylic ester. Butyl 7-hydroxy-chroman-3-carboxylic ester is coupled to various 'left' hand side molecules either by Mitsunobu reaction or Williamson ether synthesis. t-Butyl group is then deprotected to provide carboxylic acids (1) and these acids are further modified to corresponding amide or sulfonamide compounds. Homocarboxylic acid (14) is synthesized by transformation of carboxylic functional group into mesylate and subsequent nucleophilic displacement of mesylate with cyanide and hydrolysis.

These compounds are effective in lowering glucose and free fatty acid. Also these compounds showed markedly reduced insulin and glucose amount (Auc) in the ITT (insulin tolerance test) and OGTT (oral glucose tolerance test) which are the typical phenomena observed with insulin sensitizing compounds. These compounds are expected to be effective in the treatment and control of non-insulin dependent diabetes mellitus and its related complications such as nephropathy, neuropathy and retinopathy (NIDDM) in humans as well as in the treatment and control of obesity and its related disease such as hyperlipidemia, dyslipedemia, hypercholesterolemia, hypertriglycemia, atherosclerosis.

Metabolites-Prodrugs

This invention also includes active metabolites of claimed compounds. Prodrugs, which are the compounds that are converted to the claimed compounds as they are being administered to a patient or after they have been administered to a patient, are also included within the scope of the claimed active compounds. A non-limiting example of a prodrug of the carboxylic acids of this invention would be an ester of the carboxylic acid group, for example a $C_1$-$C_6$ ester, which may be linear or branched, or an ester which has functionality that makes it more easily hydrolyzed after administration to a patient. Also, amides of primary and secondary amines and various substituted amines are also included.

Administration and Dose Ranges

Any suitable route of administration may be employed for providing a mammal, especially a human, with an effective dose of a compound of the present invention. For example, oral, rectal, topical, parenteral, ocular, pulmonary, nasal and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art. When treating or preventing diabetes mellitus and/or hyperglycemia or hypertriglycemia or other diseases of which compounds of Formula I are indicated, generally satisfactory results are obtained when the compounds of the present invention are administered at a daily dosage of from about 0.1 mg-100 mg/kg of patient body weight, preferably given as a single daily dose or in divided dose 2-6 times/day, or in sustained release form. For larger mammals, the total daily dosage is from about 1 mg~1 g, preferably from about 1-50 mg. In the case of 70 kg adult human, the total daily dose will generally be from about 7 mg to 350 mg. This dosage regimen may be adjusted to provide the optional therapeutic response.

Pharmaceutical Compositions

Another aspect of the present invention provides pharmaceutical composition which comprises a compound of Formula I and a pharmaceutically acceptable carrier. The compounds of Formula I, its salts and/or its pro-drugs, for various form of administration such as oral, nasal, parenteral and other as previously described, can be combined as the active ingredients in the admixture of a pharmaceutical carrier according to conventional pharmaceutical compounding techniques. The carrier may vary depending on the dosage form and chosen from the variety of the carriers such as water, glycols, oils, alcohols, flavoring agents, preservatives, coloring agents, sweeteners and the like. Also carrier includes starches, sugars, cellulose, binders, and the like for the hard and soft capsule tablets and water, alcohol, glycerol, cellulose, oils and the like for suspensions.

Combination Therapy

Compounds of Formula I may be used in combination with other drugs that may further enhance the optimal pharmaceutical properties. The combination therapy may be used to further enhance the efficacy of the aimed disease as described earlier or to cover the broader area of the symptoms or to lower the toxicity or to enhance the pharmacokinetic properties. The preferred effects are the enhancement of the efficacy for the treatment and control of disease and complications that accompany with diabetes diseases. Examples of other active ingredients that may be administered in combination with a compound Formula I, and either administered separately or in the same pharmaceutical composition, includes, but are not limited to:

(a) insulin sensitizers including (i) biguanides such as metformin and fenformin, (ii) PPARγ agonist such as pioglitazone, rosiglitazone and englitazone, (iii) protein tyrosine phosphatase-1B (PTP-1B) inhibitors, and (iv) dipeptidyl peptidase IV inhibitors;
(b) insulin or insulin mimetics;
(c) sulfonylureas such as tolbutamide, and glyburide;
(d) α-glucosidase inhibitors;
(e) cholesterol lowering agents such as HMG-CoA reductase inhibitors (lovastatin, pravastatin, fluvastatin, atorvastatin, itavastatin, rivastatin, simvastatin, and other statins)
(f) antiobesity compounds such as fenfluramine and dexfenfluramine;
(g) cycloxygenase-2 (COX-2) inhibitors such as MBX-102; and
(h) lipase inhibitor such as orlistat.

It may be preferable to administer to treat, prevent or control atherosclerosis in a mammalian patient, of an effective amount of a compound of Formula I and an effective amount of an HMG-CoA reductase inhibitors such as statin including lovastatin, pravastatin, fluvastatin, atorvastatin, itavastatin and rivastatin.

The invention further includes pharmaceutically acceptable compositions comprising any of the compounds described above and a pharmaceutically acceptable carrier.

The following examples are provided to illustrate the invention, including methods of making the compounds of the invention, and are not to be construed as limiting the invention in any manner. The scope of the invention is defined in the appended claims.

EXAMPLES

Specific examples of compounds of this invention are provided as Examples 1-14, listed by name below, and their structures are illustrated in the Table 1.

TABLE 1

Specific examples of compounds of this invention

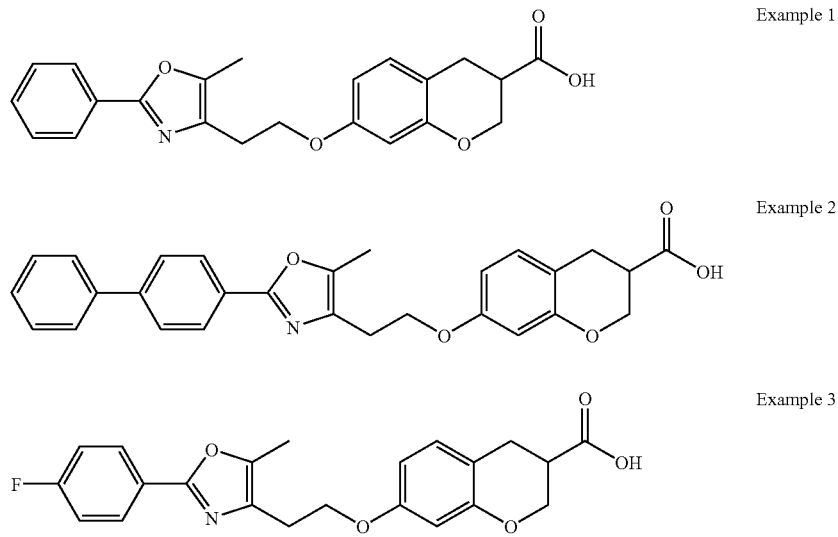

TABLE 1-continued
Specific examples of compounds of this invention
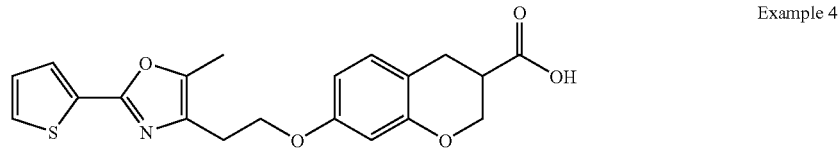
Example 4
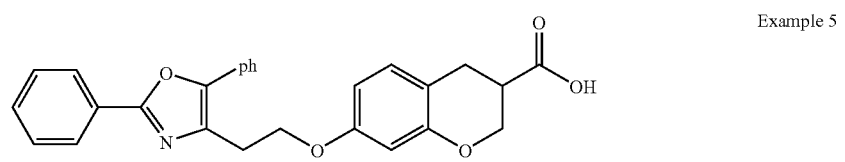
Example 5
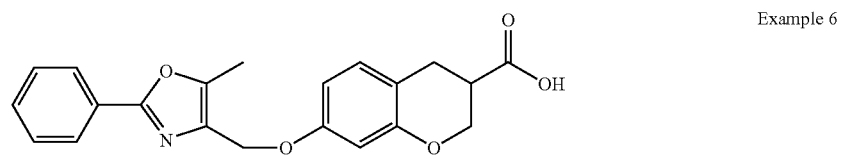
Example 6
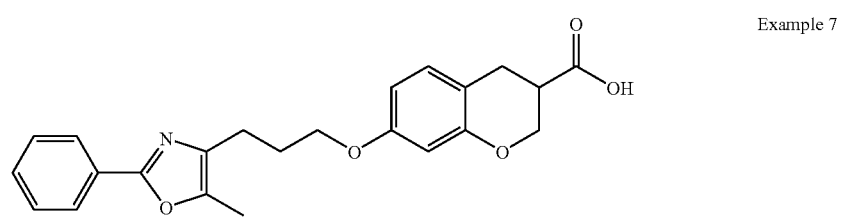
Example 7
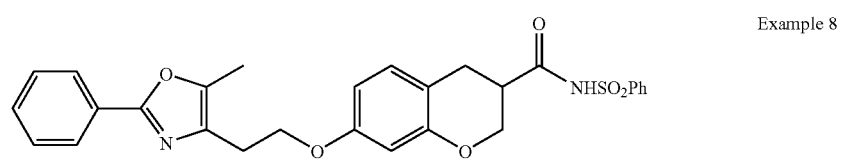
Example 8
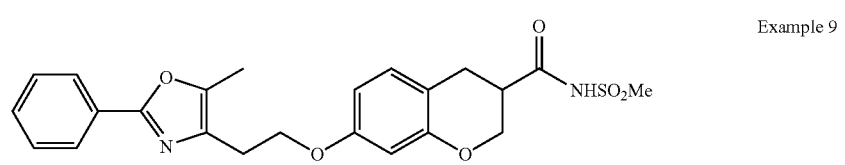
Example 9
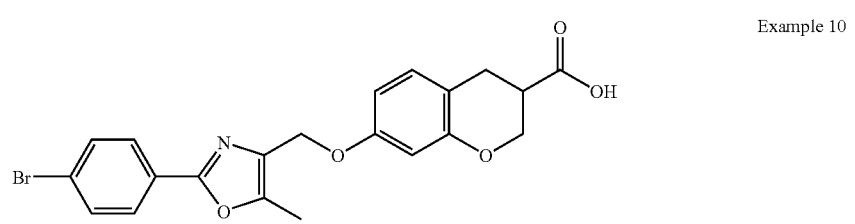
Example 10
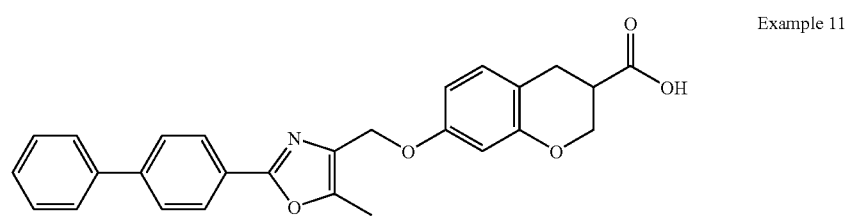
Example 11

TABLE 1-continued

Specific examples of compounds of this invention

| | |
|---|---|
| 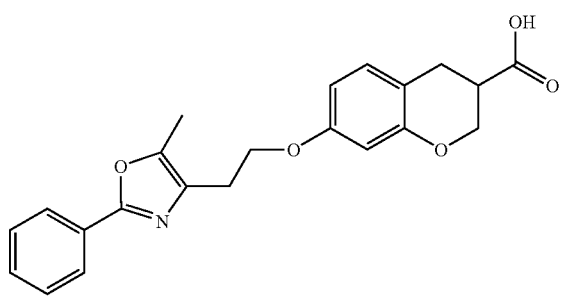 | Example 12 |
| | Example 13 |
| | Example 14 |

Example 1

Preparation of 7-[2-(5-Methyl-2-phenyl-4-oxazolyl) ethoxy]chromane-3-carboxylic acid

Step A: Preparation of tert-butyl 7-(benzyloxy)-2H-chromene-3-carboxylate having following formular

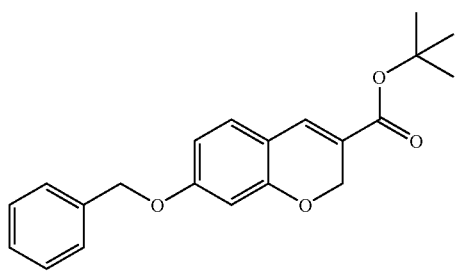

To a stirred solution of 4-benzyloxy-2-hydroxy benzaldehyde (11.41 g, 50 mmol) in NMP (30 ml) was added $K_2CO_3$ (13.0 g, 100 mmol) and heated to 155° C. under $N_2$ atmosphere. t-Butyl acrylate (36.5 ml, 250 mmol) was divided into 4 portions (10, 10, 10 & 6.5 ml). First 10 ml was added to the reaction mixture and heated at 155° C. The rest were added after 2 hr intervals and the reaction mixture was heated for total of 8 hrs. The reaction mixture was cooled to room temperature and water (150 ml) was added. The product was extracted with 150 ml of ether. The ether layer was washed with water twice and dried. Ether layer was diluted with 50% hexanes and passed through a pad of silica (3 inch length and 4 inch diameter). The silica was washed with 50% ether/hexane mixture and the solvent was evaporated to give the product as pale yellow solid (13 g, 77%).

$^1$H NMR: (300 MHz, $CDCl_3$): δ 7.43-7.38 (m, 5H), 7.06 (d, 1H), 6.57(d, 1H), 6.50 (s, 1H), 5.07 (s, 2H), 4.95 (s, 2H), 1.48 (s, 9H).

Step B: Preparation of tert-butyl 7-hydroxychromane-3-carboxylate having the following formula

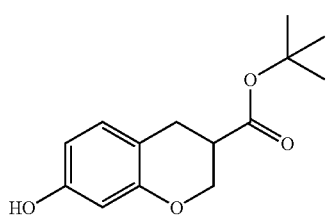

tert-butyl 7-(benzyloxy)-2H-chromene-3-carboxylate (13 g) was dissolved in ethyl acetate (15 ml) and methanol (5 ml) in a hydrogenation bottle. Pd—C (10%) (1 g) was added and the reaction mixture was hydrogenated ($H_2$, 70 psi & RT) for overnight. After the completion of the reaction, catalyst was filtered and washed with 100 ml of ethyl acetate. Solvent was evaporated and the crude product was purified using column chromatography and ethyl acetate hexane mixture to give 6 g of pure product (48.3% overall for 2 steps).

¹H NMR: (300 MHz, CDCl₃): δ 6.95 (d, 1H), 6.42 (d, 1H), 6.35 (s, 1H), 4.63 (s, 1H), 4.43-4.38 (m, 1H), 4.10-4.03 (m, 1H), 2.96-2.86 (m, 3H), 1.49 (s, 9H).

Mass m/z: 251.2 (M⁺H)

Step C: Preparation of tert-butyl-7-[2-(5-Methyl-2-phenyl-4-oxazolyl)ethoxy]chromane-3-carboxylate having the following formula

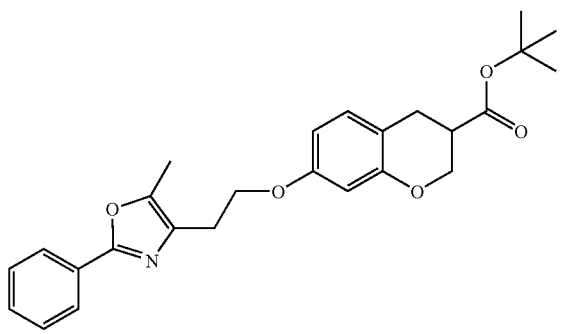

To a stirred solution of tert-butyl 7-hydroxychromane-3-carboxylate (2.5 g, 10 mmol) in CH₃CN (20 ml), K₂CO₃ (4.1 g) and 2-(5-methyl-2-phenyl-1,3-oxazol-4-yl)ethyl methanesulfonate (3.7 g) were added and the reaction mixture was heated under reflux for overnight. The reaction mixture was cooled to room temperature and diluted with 100 ml of diethyl ether. The diluted solution was passed through a pad of silica and the silica was washed with more ether. The ether solution was evaporated to dryness and purified using silica chromatography. The product was isolated as a white sold (2.8 g, 64.3%).

¹H NMR: (300 MHz, CDCl₃): δ 7.99 (d, 2H), 7.45-7.43 (m, 3H), 6.94 (d, 1H), 6.48 (d, 1H), 6.40 (s, 1H), 4.41 (t, 2H), 4.20 (t, 2H), 4.08-4.02 (m, 1H), 3.00-2.92 (m, 5H), 2.93 (s, 3H), 1.48 (s, 9H).

Step D: Preparation of 7-[2-(5-Methyl-2-phenyl-4-oxazolyl)ethoxy]chromane-3-carboxylic acid tert-butyl-7-[2-(5-Methyl-2-phenyl-4-oxazolyl)ethoxy]chromane-3-carboxylate (5.2 g, 11.95 mmol) was dissolved in 25 ml of formic acid and heated at 60° C. for 12 hrs. Formic acid was removed in vacuum pump and ether (25 ml) was added and heated for 10 minutes. The resultant suspension was cooled at −20° C. for 1 hr and filtered. The solid product was washed with 20 ml of diethyl ether and dried to give the compound 7-[2-(5-Methyl-2-phenyl-4-oxazolyl)ethoxy]chromane-3-carboxylic acid as white powder (3.8 g, 84%).

¹H NMR: (300 MHz, CDCl₃): δ 8.03-8.00 (m, 2H), 7.99-7.48 (m, 3H), 6.98 (d, 1H), 6.50 (d, 1H), 6.41 (s, 1H), 4.42 (d, 1H), 4.22-4.12 (m, 3H), 3.60-3.20 (brs, 1H), 3.09-3.02 (m, 5H), 2.43 (s, 3H).

Mass m/z: 380.1 (M⁺H)

Example 2

Preparation of 7-[2-(5-Methyl-2-(4-phenyl)phenyl-4-oxazolyl)ethoxy]chromane-3-carboxylic acid

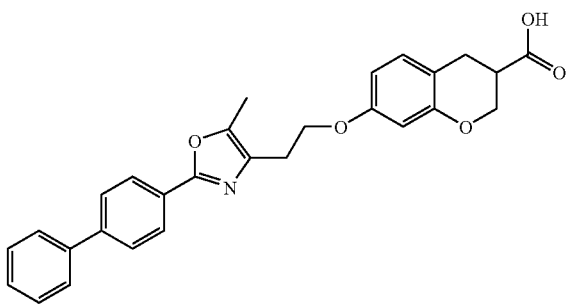

Step A: Preparation of tert-butyl-7-[2-(5-Methyl-2-(4-phenyl)phenyl-4-oxazolyl)ethoxy]chromane-3-carboxylate To a stirred solution of tert-butyl 7-hydroxychromane-3-carboxylate (500 mg, 2 mmol), triphenyl phosphine (786.8 mg, 3 mmol) and 2-(5-methyl-2-(4-phenyl)phenyl-1,3-oxazol-4-yl)ethanol (672 mg, 2.4 mmol) in toluene (10 ml) was treated slowly with diethyl azodicarboxylate (372.4 mg, 3 mmol) over a period of 10 min under nitrogen atmosphere. After the addition was completed, the reaction mixture was heated at 60° C. for 8 hrs. Toluene was removed under vacuum and the residue was purified by column chromatography on silica using 20% ethyl acetate and hexanes as eluent to give the product (550 mg, 55%).

¹H NMR: (300 MHz, CDCl₃): δ 8.07 (d, 2H), 7.71-7.65 (m, 4H), 7.49-7.37 (m, 3H), 6.96 (t, 1H), 6.43 (d, 1H), 6.35 (s, 1H), 4.42 (d, 1H), 4.22 (t, 2H), 4.04 (t, 1H), 3.02-2.90 (m, 5H), 2.42 (s, 3H), 1.48 (s, 9H)

Step B

The t-butyl ester obtained from the previous step (250 mg, 0.48 mmol) was dissolved in HCO₂H (5 ml) and heated at 40° C. for 7 hrs. Solvent was removed using vacuum pump and the residue was purified by preparative HPLC (190 mg, 87%).

¹H NMR: (300 MHz, CDCl₃): δ 10.17 (brs, 1H), 8.10 (d, 2H), 7.75 (d, 2H), 7.67 (d, 2H), 7.53-7.43 (m, 4H), 6.97 (d, 1H), 6.43 (d, 1H), 6.39 (s, 1H), 4.39 (d, 1H), 4.23-4.10 (m, 3H), 3.12-2.99 (m, 5H), 2.48 (s, 3H).

Mass m/z: 456.1(M⁺H)

Example 3

Preparation of 7-[2-(5-Methyl-2-(4-fluoro)phenyl)-4-oxazolyl]ethoxy]chromane-3-carboxylic acid

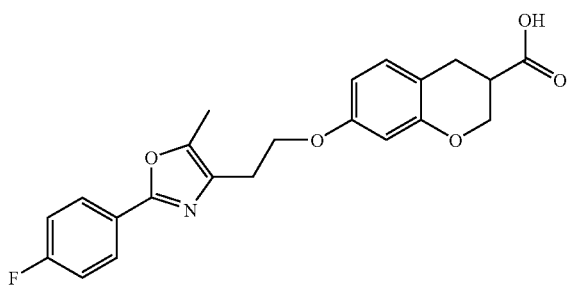

Step A: Preparation of tert-butyl-7-[2-(5-Methyl-2-(4-fluoro)phenyl)-4-oxazolyl]ethoxy]chromane-3-carboxylate To a stirred solution of tert-butyl 7-hydroxychromane-3-carboxylate (750 mg, 3 mmol), triphenyl phosphine (864 mg, 3.3 mmol) and 2-(5-methyl-2-(4-fluoro)phenyl-1,3-oxazol-4-yl)ethanol (752 mg, 3.3 mmol) in toluene (10 ml) was treated slowly with diethyl azodicarboxylate (574.5 mg, 3.3 mmol) over a period of 10 min under nitrogen atmosphere. After the addition was complete, the reaction mixture was heated at 60° C. for 17 hrs. Toluene was removed under vacuum and the residue was purified by column chromatography on silica using 20% ethyl acetate and hexanes as eluent to give the product (510 mg, 36%).

$^1$H NMR: (300 MHz, CDCl$_3$): δ 8.01-7.96 (m, 2H), 7.15 (d, 2H), 6.97 (d, 1H), 6.48 (d, 1H), 6.41 (s, 1H), 4.40 (d, 1H), 4.20 (t, 2H), 4.04 (t, 1H), 2.99-2.88 (m, 5H), 2.39 (s, 3H), 1.48 (s, 9H).

Step B

The t-butyl ester obtained from the previous step (250 mg, 0.55 mmol) was dissolved in HCO$_2$H (5 ml) and heated at 40° C. for 6 hrs. Solvent was removed using vacuum pump and the residue was purified by preparative HPLC (197 mg, 90%).

$^1$H NMR: (300 MHz, CDCl$_3$): δ 8.01-7.97 (m, 2H), 7.14 (t, 2H), 6.98 (d, 1H), 6.51 (d, 1H), 6.43 (s, 1H), 4.41 (d, 1H), 4.21-4.11 (m, 3H), 3.06-2.95 (m, 5H), 2.39 (s, 3H).

Mass m/z: 398.2 (M$^+$H)

Example 4

Preparation of 7-[2-(5-methyl-2-thien-2-yl-1,3-oxazol-4-yl)ethoxy]chromane-3-carboxylic acid

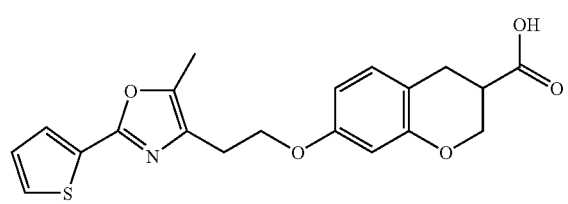

Step A: Preparation of tert-butyl-7-[2-(5-methyl-2-thien-2-yl-1,3-oxazol-4-yl)ethoxy]chromane-3-carboxylic acid 2-(5-methyl-2-thien-2-yl-1,3-oxazol-4-yl)ethyl methanesulfonate (947 mg, 3.3 mmol), tert-butyl 7-hydroxychromane-3-carboxylate (750 mg, 3 mmol) and potassium carbonate (1.24 g, 9 mmol) were mixed in CH$_3$CN and refluxed under N$_2$ atmosphere overnight. After the completion of the reaction (TLC), the reaction mixture was cooled to room temperature and diluted with 30 ml of diethyl ether and passed through a small pad of silica. Silica was washed with 100 ml of ether and the ether solution was evaporated to give the product which was purified by column chromatography on silica using ethyl acetate and hexanes as eluent (699 mg, 53%).

$^1$H NMR: (300 MHz, CDCl$_3$): δ 7.60 (d, 1H), 7.39 (t, 1H), 7.11 (d, 1H), 6.96 (d, 1H), 6.47 (d, 1H), 6.40 (s, 1H), 4.40 (d, 1H), 4.21-4.16 (m, 3H), 4.04 (t, 1H), 2.98-2.93 (m, 5H), 2.38 (s, 3H), 1.48 (s, 9H).

Step B: Preparation of 7-[2-(5-methyl-2-thien-2-yl-1,3-oxazol-4-yl)ethoxy]chromane-3-carboxylic acid The tert-butyl ester from the previous step (400 mg, 0.9 mmol) was converted to free acid (320 mg, 91%) by previously described procedure in Example 1, Step D.

$^1$H NMR: (300 MHz, DMSO-D6): δ 7.74 (d, 1H), 7.61 (d, 1H), 7.18 (d, 1H), 6.99 (d, 1H), 6.45 (d, 1H) 6.33 (s, 1H), 4.30 (d, 1H), 4.14-4.05 (m, 3H), 2.95-2.85 (m, 5H), 2.34 (s, 3H).

Mass m/z: 386.2 (M$^+$H)

Example 5

Preparation of 7-[2,5 diphenyl-4-oxazolyl]ethoxy]chromane-3-carboxylic acid

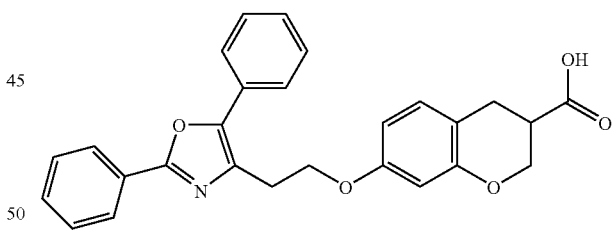

Step A: Preparation of tert-butyl-7-[2,5 diphenyl-4-oxazolyl]ethoxy]chromane-3-carboxylate To a stirred solution of tert-butyl 7-hydroxychromane-3-carboxylate (750 mg, 3 mmol), triphenyl phosphine (1.1 g, 4.5 mmol) and 2,5-diphenyl-(1,3-oxazol-4-yl)ethanol (946 mg, 3.6 mmol) in toluene (15 ml) was treated slowly with diethyl azodicarboxylate (783 mg, 4.5 mmol) over a period of 10 min under nitrogen atmosphere. After the addition was complete, the reaction mixture was heated at 60° C. for 19 hrs. Toluene was removed under vacuum and the residue was purified by column chromatography on silica using 20% ethyl acetate and hexanes as eluent to give the product (450 mg, 29.4%).

¹H NMR: (300 MHz, CDCl₃): δ 8.12 (d, 2H), 7.82 (d, 2H), 7.53-7.36 (m, 6H), 6.97 (d, 1H), 6.48 (d, 1H), 6.43 (s, 1H), 4.41-4.4=32 (m, 3H), 4.03 (t, 1H), 3.31 (t, 2H), 2.96-2.86 (m, 3H), 1.48 (s, 9H).

Step B: Preparation of 7-[2,5 diphenyl-4-oxazolyl)ethoxy]chromane-3-carboxylic acid The tert-butyl ester from the previous step (300 mg, 0.58 mmol) was converted to free acid (210 mg, 81%) by previously described procedure in Example 1, step D.

¹H NMR: (300 MHz, CDCl₃): δ 8.11 (d, 2H), 7.81 (d, 2H), 7.52-7.36 (m, 6H), 6.97 (d, 1H), 6.51 (d, 1H), 6.45 (s, 1H), 4.44-4.35 (m, 3H), 4.17 (t, 1H), 3.32 (t, 2H), 3.06-2.96 (m, 3H).

Mass (m/z): 442.2 (M⁺H)

Example 6

Preparation of 7-[(2-phenyl-5-methyl-1,3-oxazol-4-yl)methoxy]chromane-3-carboxylic acid

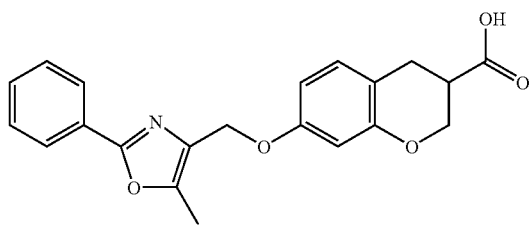

Step A: Preparation of tert-butyl-7-[(2-phenyl-5-methyl-1,3-oxazol-4-yl)methoxy]chromane-3-carboxylate To a stirred solution of 4-(chloromethyl)-5-methyl-2-phenyl-1,3-oxazole (103.5 mg, 0.5 mmol) and potassium carbonate (138.4 mg, 1 mmol), tert-butyl 7-hydroxychromane-3-carboxylate (125 mg, 0.5 mmol) was added and the reaction mixture was stirred at room temperature for 48 hrs. Water (50 ml) was added and the precipitated product was extracted with 25 ml of diethyl ether. Ether layer was washed with water (25 ml) twice and dried. On evaporation of solvent, the product was obtained as pale yellow gum (150 mg, 36%).

¹H NMR: (300 MHz, CDCl₃): δ 8.02 (d, 2H), 7.54 (s, 3H), 7.02 (d, 1H), 6.55 (d, 1H), 6.48 (s, 1H), 5.04 (s, 2H), 4.41 (d, 1H), 4.40 (t, 1H), 3.02-2.80 (m, 3H), 2.50 (s, 3H).

Step B: Preparation of 7-[(2-phenyl-5-methyl-1,3-oxazol-4-yl)methoxy]chromane-3-carboxylic acid The tert-butyl ester from the previous step (100 mg, 0.24 mmol) was converted to free acid (76 mg, 88%) by previously described procedure in Example 1, Step D.

¹H NMR: (300 MHz, CDCl₃): δ 8.04 (d, 2H), 7.48-7.47 (m, 3H), 7.02 (d, 1H), 6.60 (d, 1H), 6.52 (s, 1H), 4.96 (s, 2H), 4.43 (d, 1H), 3.99 (t, 1H), 3.80-3.50 (brs, 1H), 3.08-2.80 (m, 3H), 2.47 (s, 3H).

Mass m/z: 366.0 (M⁺H)

Example 7

Preparation of 7-[3-(5-Methyl-2-phenyl-4-oxazolyl)propoxy]chromane-3-carboxylic acid

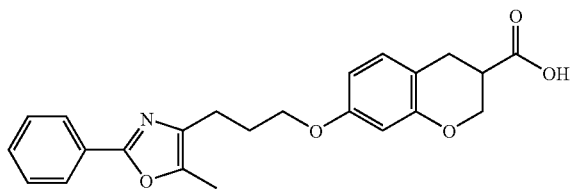

Step A: Preparation of tert-butyl-7-[3-(5-Methyl-2-phenyl-4-oxazolyl)propoxy]chromane-3-carboxylate To a stirred solution of tert-butyl 7-hydroxychromane-3-carboxylate (250 mg, 1 mmol) in CH₃CN (10 ml), K₂CO₃ (414 mg) and 3-(5-methyl-2-phenyl-1,3-oxazol-4-yl)propyl methanesulfonate (325 mg) were added and the reaction mixture was heated under reflux for overnight. The reaction mixture was cooled to room temperature and diluted with 30 mL of diethyl ether. The diluted solution was passed through a pad of silica and the silica was washed with more ether. The ether solution was evaporated to dryness and purified using silica chromatography. The product was isolated as a white sold (397 mg, 88%).

¹H NMR: (300 MHz, CDCl₃): δ 8.05 (d, 2H), 7.55 (t, 2H), 6.98 (d, 1H), 6.46 (d, 1H), 6.37 (s, 1H), 4.40 (d, 1H), 4.06 (t, 1H), 3.93 (t, 2H), 2.96-2.85 (m, 5H), 2.37 (s, 3H), 2.20-2.12 (m, 2H), 1.46 (s, 9H).

Step B: Preparation of 7-[3-(5-Methyl-2-phenyl-4-oxazolyl)propoxy]chromane-3-carboxylic acid The tert-butyl ester from the previous step (10 mg, 0.22 mmol) was converted to free acid (89 mg, 100%) by previously described procedure in Example 1, Step D.

¹H NMR: (300 MHz, CDCl₃): δ 8.00 (d, 2H), 7.44 (t, 3H), 6.98 (d, 1H), 6.51 (d, 1H), 6.41 (s, 1H), 4.42 (d, 1H), 4.15 (t, 1H), 3.95 (t, 2H), 3.07-3.03 (m, 3H), 2.71 (t, 2H), 2.71 (s, 3H), 2.14 (p, 2H).

Mass (m/z): 394.2 (M⁺H)

Example 8

Preparation of 7-[(2-phenyl-5-methyl-1,3-oxazol-4-yl)methoxy]N-(phenylsulfonyl)chromane-3-carboxamide

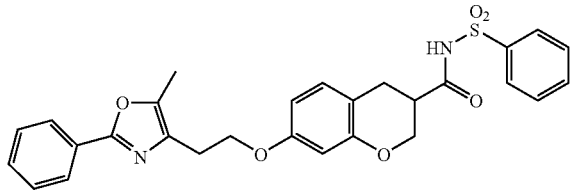

To a stirred solution of benzene sulfonamide (760 mg, 5 mmol), dimethylaminopyridine (134 mg, 1.1 mmol) and 7-[2-(5-methyl-2-phenyl-4-oxazolyl)ethoxy]chromane-3- carboxylic acid (379 mg, 1 mmol) was added to diisopropyl carbodiimide (0.234 ml, 1.5 mmol) and the reaction mixture was stirred overnight at room temperature in dichloromethane (5 ml). CH$_2$Cl$_2$ was removed and the residue was dissolved in acetone (5 ml) and filtered. The filtrate was directly purified by preparative LCMS (189 mg, 36.4%).

$^1$H NMR: (300 MHz, CDCl$_3$): δ 8.84 (brs, 1H), 7.99-7.97 (m, 5H), 7.66-7.44 (m, 5H), 6.89 (d, 1H), 6.50 (d, 1H), 6.40 (s, 1H), 4.29-4.06 (m, 4H), 3.03-2.85 (m, 5H), 2.41 (s, 3H).

Mass m/z: 519.0 (M$^+$H)

Example 9

Preparation of 7-[(2-phenyl-5-methyl-1,3-oxazol-4-yl)methoxy]N-(methylsulfonyl)chromane-3-carboxamide

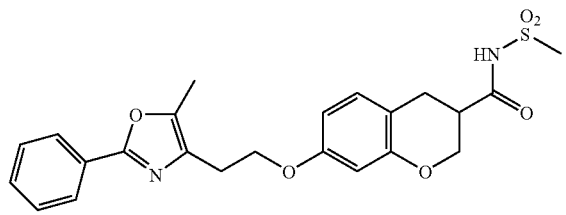

To a stirred solution of methane sulfonamide (475 mg, 5 mmol), dimethylaminopyridine (134 mg, 1.1 mmol) and 7-[2-(5-methyl-2-phenyl-4-oxazolyl)ethoxy]chromane-3-carboxylic acid (379 mg, 1 mmol) was added diisopropyl carbodiimide (0.234 ml, 1.5 mmol) and the reaction mixture was stirred overnight at RT in dichloromethane (5 ml). CH$_2$Cl$_2$ was removed and the residue was dissolved in acetone (5 ml) and filtered. The filtrate was directly purified by preparative LCMS (260 mg, 57%).

$^1$H NMR: (300 MHz, CDCl$_3$): δ 8.27 (s, 1H), 8.01 (d, 2H), 7.47 (t, 3H), 6.99 (d, 1H), 6.53 (d, 1H), 6.43 (s, 1H), 4.33-4.20 (m, 4H), 3.30 (s, 3H), 3.07-2.94 (m, 5H), 2.43 (s, 3H)

Mass m/z: 457.0 (M$^+$H)

Example 10

Preparation of 7-[(2-(4-bromophenyl)-5-methyl-1,3-oxazol-4-yl)methoxy]chromane-3-carboxylic acid

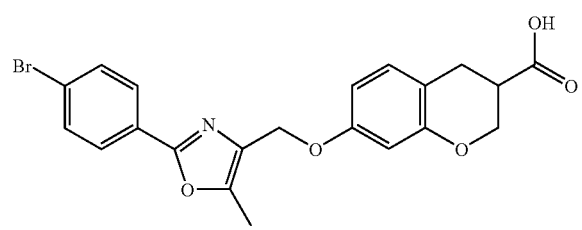

Step A: Preparation of tert-butyl-7-[(2-(4-bromophenyl)-5-methyl-1,3-oxazol-4-yl)methoxy]chromane-3-carboxylate To a stirred suspension of tert-butyl 7-hydroxychromane-3-carboxylate (1.1 g, 4.4 mmol) and potassium carbonate (1.1 g, 8 mmol), 2-(4-bromophenyl)-4-(chloromethyl)-5-methyl-1,3-oxazole (1.14 g, 4 mmol) was added and the reaction mixture was stirred at 60° C. for overnight. After the completion of the reaction, water (40 ml) was added and the precipitated product was extracted with ethylacetate (60 ml). The organic layer was washed with 50 ml of water twice and dried. The dried solution was evaporated to give the product as brown solid (1.55 g, 77.4%).

$^1$H NMR: (300 MHz, CDCl$_3$): δ 7.90 (d, 2H), 7.59 (d, 2H), 7.00 (d, 1H), 6.54 (d, 1H), 6.51 (s, 1H), 4.94 (s, 2H), 4.42 (d, 1H), 4.07 (t, 1H), 2.95-2.75 (m, 3H), 2.45 (s, 3H), 1.49 (s, 9H).

Step B: Preparation of 7-[(2-(4-bromophenyl)-5-methyl-1,3-oxazol-4-yl)methoxy]chromane-3-carboxylic acid The tert-butyl ester from the previous step (500 mg, 1 mmol) was converted to free acid (389 mg, 86%) by previously described procedure in Example 1, Step D.

$^1$H NMR: (300 MHz, CDCl$_3$): δ 7.90 (d, 2H), 7.62 (d, 2H), 7.02 (d, 1H), 6.59 (t, 1H), 6.51 (s, 1H), 4.96 (s, 2H), 4.44 (dd, 1H), 4.12 (t, 1H), 3.32 (brs, 1H), 3.06-3.01 (m, 3H), 2.46 (s, 3H).

Mass m/z: 445.8 (M$^+$H)

Example 11

Preparation of 7-[(2-(4-phenyl)-phenyl)-5-methyl-1,3-oxazol-4-yl]methoxy]chromane-3-carboxylic acid

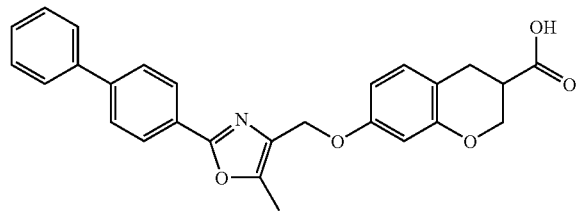

Step A: Preparation of tert-butyl-7-[(2-(4-phenyl)-phenyl)-5-methyl-1,3-oxazol-4-yl]methoxy]-chromane-3-carboxylate To a stirred solution of tert-butyl-7-[(2-(4-bromophenyl)-5-methyl-1,3-oxazol-4-yl)methoxy]chromane-3-carboxylate (501 mg, 1 mmol), triphenylphosphine (4.7 mg, 0.018 mmol), Palladium(II)acetate (1.3 mg, 0.006 mmol) and phenylboronic acid (130 mg, 1.1 mmol) in 1-propanol (3 ml) was added Na$_2$CO$_3$ (137 mg, 1.3 mmol) in 1 ml of water. The reaction mixture was refluxed under N$_2$ atmosphere for 4 hrs. After the completion of the reaction, water and propanol were removed and the residue was dissolved in 50 ml of ethyl acetate. The ethylacetate solution was washed with water (100 ml) and then dried. Evaporation of ethyl acetate gave the product as black solid (400 mg, 80.4%).

$^1$H NMR: (300 MHz, CDCl$_3$): δ 8.11 (d, 2H), 7.72-7.66 (m, 4H), 7.50 (t, 1H), 7.42 (d, 1H), 7.02 (d, 1H), 6.60 (d, 1H), 6.53 (s, 1H), 4.97 (s, 1H), 4.44 (t, 1H), 4.08 (t, 1H), 2.95-2.91 (m, 3H), 2.47 (s, 3H), 1.42 (s, 9H).

Step B: Preparation of 7-[(2-(4-phenyl)-phenyl)-5-methyl-1,3-oxazol-4-yl)methoxy]chromane-3-carboxylic acid The tert-butyl ester from the previous step (250 mg, 0.5 mmol) was converted to free acid (170 mg, 77%) by previously described procedure in Example 1, Step D.

$^1$H NMR: (300 MHz, DMSO-D$_6$): δ 8.03 (d, 2H), 7.84 (d, 1H), 7.75 (d, 2H), 7.53 (t, 3H), 7.42 (d, 1H), 7.03 (d, 1H), 6.56 (d, 1H), 6.48 (s, 1H), 4.94 (s, 2H), 4.30 (s, 1H), 4.11 (t, 1H), 3.03-2.89 (m, 3H), 2.46 (s, 3H).

Mass m/z: 442.2 (M$^+$H)

Example 12

Preparation of Methyl 7-[2-(5-Methyl-2-phenyl-4-oxazolyl)ethoxy]chromane-3-carboxylate

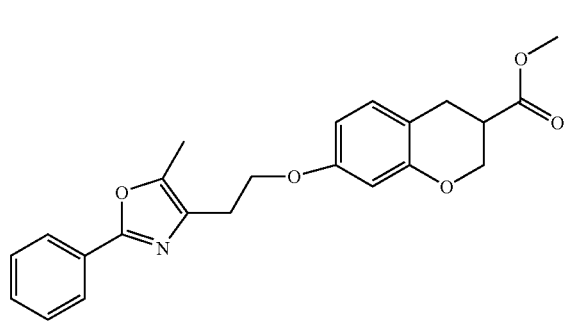

To a stirred solution of 7-[2-(5-methyl-2-phenyl-4-oxazolyl)ethoxy]chromane-3-carboxylic acid (189.5 mg, 0.5 mmol) was suspended in MeOH (10 ml). SOCl$_2$ (0.5 ml) was added drop wise over 5 min. The resultant solution was stirred overnight. MeOH was evaporated and the product was dissolved in CH$_2$Cl$_2$ (25 ml). The solution was washed with sat. NaHCO$_3$ (10 ml), dried and evaporated to give the methyl ester as pale yellow solid (139 mg, 71%).

$^1$H NMR: (300 MHz, CDCl$_3$): δ 8.00 (d, 2H), 7.46 (t, 3H), 6.98 (d, 1H), 6.49 (d, 1H), 6.41 (s, 1H), 4.43 (t, 1H), 4.23-4.11 (m, 3H), 3.76 (s, 3H), 3.04-2.95 (m, 5H), 2.40 (s, 3H).

Mass m/z: 394.3 (M$^+$H)

Example 13

Preparation of 7-[2-(5-Methyl-2-phenyl-4-oxazolyl)ethoxy]chromane-3-carboxylic acid amide

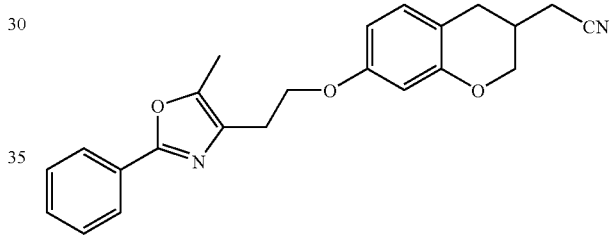

7-[2-(5-Methyl-2-phenyl-4-oxazolyl)ethoxy]chromane-3-carboxylic acid (189.5 mg, 0.5 mmol) was dissolved in CH$_2$Cl$_2$ (5 ml) and thionyl chloride (0.109 ml, 1.5 mmol) was added under N$_2$ atmosphere. The resulting suspension was stirred until all the acid dissolved (2 hr). Solvent acid was removed in a rotary evaporator and the residue was dissolved in 5 ml of THF. NH$_3$ (aq, 35%, 5 ml) was added and stirred for 4 hrs. After evaporation of THF, the residue was partitioned between water (10 ml) and EtOAc (20 ml). The organic layer was washed with 5 ml saturated NaHCO$_3$ and dried over Na$_2$SO$_4$. On evaporation of EtOAC, the product wad obtained as white solid (160 mg, 85%).

$^1$H NMR: (300 MHz, CDCl$_3$): δ 8.05 (d, 2H), 7.63-7.46 (m, 3H), 6.96 (d, 1H), 6.49 (d, 1H), 6.42 (s, 1H), 5.77 (brs, 1H), 5.44 (brs, 1H), 4.38-4.14 (m, 4H), 3.10-2.81 (m, 5H), 2.07 (s, 3H).

Mass m/z: 379(M$^+$H)

Example 14

Preparation of {7-[2-(5-Methyl-2-phenyl-oxazol-4-yl)-ethoxy]-chroman-3-yl}-acetic acid

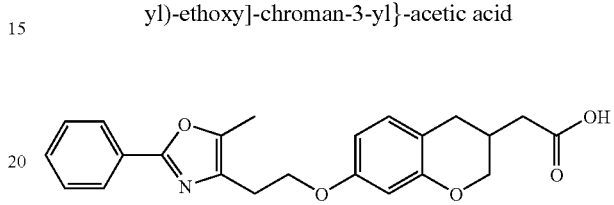

Step A: Preparation of {7-[2-(5-Methyl-2-phenyl-oxazol-4-yl)-ethoxy]-chroman-3-yl}acetonitrile To a stirred solution of 7-[2-(5-Methyl-2-phenyl-4-oxazolyl)ethoxy]chroman-3-carboxylic acid (908 mg, 2.40 mmol, 1.0 eq) in THF was added borane-THF (1M in THF, 2.63 ml, 1.1 eq) dropwise at −5° C. 4 h later, additional borane-THF (1M in THF, 2.63 ml, 1.1 eq) was added to reaction mixture at room temperature and stirred overnight. Methanol (2 ml) was added to reaction mixture and solvent was evaporated in vacuo. The residue was dissolved in EtOAc and washed with sat. NaHCO$_3$ solution followed by brine. The combined EtOAc layer was dried (Na$_2$SO$_4$), filtered and concentrated to give the alcohol (884 mg).

Mass m/z: 366.0 (M$^+$H).

To a stirred solution of alcohol (140 mg, 0.38 mmol, 1.0 eq) dissolved in MC (10 ml), was added triethylamine (0.08 ml, 0.58 mmol, 1.5 eq) at 5° C. followed by methanesulfonyl chloride (0.036 ml, 0.46 mmol, 1.2 eq). After 1 h stirring at room temperature, the reaction was quenched with water (5 ml) and the reaction mixture was extracted with MC (20 ml×2). The combined organic layer was dried (Na$_2$SO$_4$), filtered and concentrated in vacuo to give the crude mesylate (180 mg).

Mass m/z: 444.0 (M$^+$H).

A solution of mesylate (134 mg, 0.30 mmol, 1.0 eq) dissolved in dry DMSO (5 ml) was mixed with NaCN (103 mg, 7 eq) and stirred at 80° C. for 3 hrs. The reaction mixture was diluted with Et$_2$O (50 ml) and it was washed with brine (50 ml). The organic layer was dried (Na$_2$SO$_4$), concentrated in vacuo. The residue was purified with column-chromatography (hex:EtOAc=7:3) to give 68 mg (61%) of the product.

Mass m/z: 375 (M+H)

Step B: Preparation of {{7-[2-(5-Methyl-2-phenyl-oxazol-4-yl)-ethoxy]-chroman-3-yl}-acetic acid To a stirred solution of {7-[2-(5-methyl-2-phenyl-oxazol-4-yl)-ethoxy]chroman-3-yl}acetonitrile (68 mg, 0.18 mmol, 1.0 eq) was suspended in 3 ml 10% NaOH followed by additional NaOH (1 g). The reaction mixture was refluxed overnight and acidified to pH=5 with 1 N HCl. The mixture was extracted with EtOAc and concentrated in vacuo. The residue was purified using reverse preparative liquid chromatography (C-18 column, 50 mm diameter×150 mm length, $CH_3CN$ (0.1% TFA): 15 to 100% in 10 min, 25 mL/min). The fractions containing the carboxylic compound were lyophilized to give the product as a white solid (9 mg, 23%).

$^1$H NMR: (300 MHz, $CDCl_3$): δ 8.0 (m, 2H), 7.45 (d, 2H), 6.90 (d, 1H), 6.40 (m, 4H), 4.35 (m, 3H), 3.90 (m, 1H), 3.00 (m, 3H), 2.50 (m, 7H)

Mass m/z: 394.1 (M+H)

Example 15

Biological Assays

Insulin resistance is a basic etiological factor for type II diabetes. The insulin resistant state at the peripheral level causes impaired glucose utilization, which is further linked to a wide spectrum of other pathophysiologic conditions such as hyperglycemia, hyperinsulinemia, dyslipidemia, obesity and the like described previously. Compounds of Formula I were tested for glucose uptake (3T3-L1 adipocytes), blood glucose lowering (db/db), oral glucose tolerance and insulin tolerance (high fat diet rat) as described in the followings.

a) Glucose Transport Assay

3T3-L1 fibroblasts (American Type Culture Collection) were plated and grown for 2 days postconfluence in Dulbecco's modified Eagle's medium (DMEM; 4,500 mg/L glucose, HyClone) supplemented 10% FBS, 10 μg/mL penicillin and streptomycin in an atmosphere of 5% $CO_2$ at 37° C. Adipocyte differentiation was then induced using standard protocol. After 48 hr, the differentiation medium was replaced with maintenance medium containing DMEM supplemented with 10% FBS. The maintenance medium was changed every 3 days until the cells were utilized for experimentation. Glucose transport activity was measured in the presence or absence of insulin and the protocol was modified from Kletzien, R F et al. (1992) Molecular Pharmacology 41:393-398. Briefly, differentiated 3T3-L1 adipocytes were incubated with vehicle (DMSO), insulin (100 nM) alone, test compound (50 μM) alone and a combination of insulin (100 nM)+test compound (50 μM) for 48 hr. Medium was changed twice a day in the presence of compound. Glucose uptake was measured using 2-Deoxy-D-[1–$^3$H] glucose as label after 90 min incubation with each compound. The separate treatment of 50 μM of test compound and 100 nM of insulin showed the increase in glucose transport. However, glucose transport activity was significantly increased by the addition of 50 μM of test compound in the presence of 100 nM of insulin as shown in FIG. 1 indicating a synergistic effect of this compound.

TABLE 2

Effect of compounds of Formula I on 2-deoxy-D-glucose uptake in differentiated 3T3-L1 adipocytes

| | Fold Stimulation (50 μM) | |
|---|---|---|
| Compound | Compound only | Insulin* + Compound |
| Pioglitazone (reference compound) | 1.9 | 7.6 |
| 7-[2-(5-Methyl-2-phenyl-4-oxazolyl)ethoxy]chromane-3-carboxylic acid (Example 1) | 1.3 | 8.4 |
| 7-[2-(5-Methyl-2-(4-phenyl)phenyl-4-oxazolyl)ethoxy]chromane-3-carboxylic acid (Example 2) | 1.5 | 6.4 |
| 7-[2-(5-Methyl-2-(4-fluoro)phenyl)-4-oxazolyl]ethoxy]-chromane-3-carboxylic acid (Example 3) | 1.3 | 5.9 |
| 7-[2-(5-methyl-2-thien-2-yl-1,3-oxazol-4-yl)ethoxy]chromane-3-carboxylic acid (Example 4) | 1.5 | 7.6 |
| 7-[2,5 diphenyl-4-oxazolyl]ethoxy]chromane-3-carboxylic acid. (Example 5) | 1.7 | 8.1 |
| 7-[(2-phenyl-5-methyl-1,3-oxazol-4-yl)methoxy]chromane-3-carboxylic acid (Example 6) | 1.4 | 10.7 |
| 7-[3-(5-Methyl-2-phenyl-4-oxazolyl)propoxy]chromane-3-carboxylic acid (Example 7) | 1.4 | 6.5 |
| 7-[(2-phenyl-5-methyl-1,3-oxazol-4-yl)methoxy]N-(phenylsulfonyl)chromane-3-carboxamide (Example 8) | 1.5 | 8.8 |
| 7-[(2-phenyl-5-methyl-1,3-oxazol-4-yl)methoxy]N-(methylsulfonyl)chromane-3-carboxamide (Example 9) | 1.2 | 6.2 |
| 7-[(2-(4-bromophenyl)-5-methyl-1,3-oxazol-4-yl)methoxy]chromane-3-carboxylic acid (Example 10) | 1.0 | 5.1 |
| 7-[(2-(4-phenyl)-phenyl)-5-methyl-1,3-oxazol-4-yl]methoxy]chromane-3-carboxylic acid (Example 11) | 1.3 | 4.6 |
| Methyl 7-[2-(5-Methyl-2-phenyl-4-oxazolyl)ethoxy]chromane-3-carboxylate (Example 12) | 1.1 | 6.0 |
| 7-[2-(5-Methyl-2-phenyl-4-oxazolyl)ethoxy]chromane-3-carboxylic acid amide (Example 13) | 1.7 | 8.8 |
| {7-[2-(5-Methyl-2-phenyl-oxazol-4-yl)-ethoxy]-chroman-3-yl}-acetic acid (Example 14) | 1.4 | 6.9 |

Figure 2:
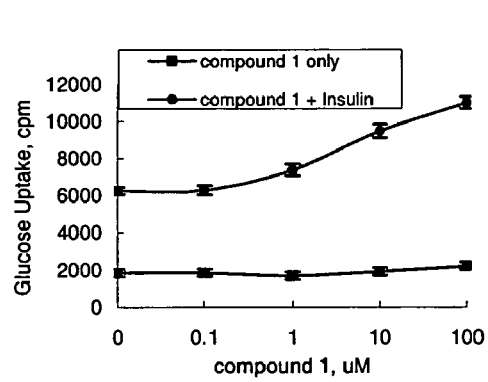
FIG. 2 illustrates an effect of compound of this invention on 2-deoxy-D-glucose uptake in dose-dependent manner in the range of 0-100 μM of the compound in the presence of 100 nM of insulin.
Figure 3:
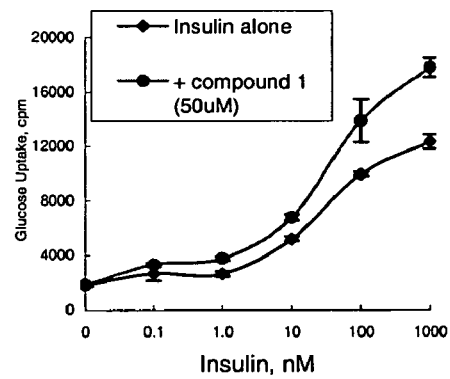
FIG. 3 illustrates an effect of compound of this invention on 2-deoxy-D-glucose uptake in dose-dependent manner in the range of 0.1-1,000 nM of insulin in the presence of 50 μM of the compound.

*100 nM of insulin was used and the insulin effect on 2-deoxy-D-glucose uptake was less than 4.0 fold In the series of compounds, one of the best result was obtained with 7-[2-(5-methyl-2-phenyl-4-oxazolyl)-ethoxy]-chroman-3-carboxylic acid (Example 1). This Compound showed glucose uptake in dose-dependent manner in the range of 0-100 μM in the presence of 100 nM of insulin (FIG. 2). Significantly, the compound of Example 1 per se did not stimulate the basal glucose uptake in 3T3-L1 adipocytes (1,850 cpm to 2,213 cpm for 0.1 to 100 μM of the compound of Example 1) and maintained at similar level of vehicle control (1,841 cpm), which proves the sensitizing activity of the compound. Also, presence of the compound of Example 1 (50 μM) further enhanced glucose uptake of insulin in dose dependent manner in the range of 0.1-1,000 nM of insulin (FIG. 3), which further assess the insulin sensitizing effect of the compound in 3T3-L1 adipocytes.

b) Efficacy Test for Blood Glucose Lowering (db/db Mice)

Mice used in this study were standard model of type II diabetes developed by Jackson Laboratories (Bar Harbor, Me.). Male, 8-week-old db/db mice were housed six per cage in hanging wire bottom cages with standard laboratory conditions. The mice had free access to normal chow (Purina Rodent Chow) and water. At the age of 11-12 weeks, mice were bled in the tail for glucose matching among the groups (n=6 per group). The grouped mice were then dosed orally with vehicle (CMC) or with compounds of formula I (30 mg/kg/d) for 7 days. Compound of formula I at 30 mg/kg/d was dosed as suspension in 0.5% CMC+0.2% Tween 80 in $H_2O$. Fresh suspension was prepared for 8 days dosing and kept in a refrigerator. The suspension was administered by oral gavage daily in the morning. The control group received vehicle (dose 10 mL/kg). Blood glucose concentrations were monitored at basal and 3 hr post dose on day 4 and 8. For blood sampling, mice were placed in a restrainer and drop of blood was obtained by nick in the tip of the tail. Blood glucose concentrations were determined either by putting a drop of blood on a glucose strip for analysis by a glucometer or using a 10 μL plasma sample in a YSI (Yellow Spring Instruments, OH) analyzer. Results are expressed as absolute blood glucose concentrations (mg/dL) and % reduction that is achieved reduction relative to vehicle treated control group. Animals having more than 300 mg/dL of blood glucose were used for testing. Statistical significance ($p<0.05$) is given versus the appropriate sample in vehicle treated animals. On day 7, the mice were fasted overnight for 18 hrs and were bled in the tail for the glucose level checking then dosed with the testing compounds (30 mg/kg/d). After 2 hr, blood samples were taken and the rats were dosed with 10% glucose in water (10 ml/kg) orally and blood glucose was monitored at 15, 30, 60, 90 and 120 min after dosing. The blood samples were centrifuged and plasma samples were collected and analyzed for insulin, Tg and FFA.

TABLE 3

Blood glucose lowering efficacy of compound of formula 1 in db/db mice

| Compound | Glucose Observed value (mg/dl) | Max % efficacy | Insulin % reduction | Fatty acid % reduction |
|---|---|---|---|---|
| Control | 261.2 | — | — | — |
| Example 1 | 132.2 | 80.0 | −62.4 | −33.7 |
| Example 2 | 148.3 | 70.3 | −72.7 | −21.1 |

It appeared that compounds of Examples 1 and 2 were not soluble in 0.5% CMC vehicle. Microemulsion of compound of Example 1, however, increased the efficacy to 114% (8 day, 5 mg/kg) in db/db mice (data not shown).

c) Oral Glucose Tolerance Test

An Oral Glucose Tolerance Test (OGTT) was performed both in db/db mice and in high fat (HF) rats after dosing 30 mg/kg/d of compounds of Examples 1 and 2 for 9 days. For OGTT and ITT studies, Sprague-Dawley rats were prepared by feeding high fat (HF) diet (60% calorie from fat) for 6 weeks. Before the study, they were matched into groups on the basis of blood glucose levels. The results are shown in the following Table 4.

TABLE 4

AUC for glucose levels during OGTT treated with compounds of Examples 1 and 2

| Compound | AUC of Glucose in db/db Observed value (mg/dl × 120 min) | % reduction | AUC of Glucose in high fat rat Observed value (mg/dl × 120 min) | % reduction |
|---|---|---|---|---|
| Control | 40858 | — | 14053 | — |
| Example 1 | 28870 | 41.5 | 12206 | 13.1 |
| Example 2 | 32406 | 14.0 | 12631 | 10.1 | d) Insulin Tolerance Test (ITT)

Insulin tolerance test (ITT) was performed in HF rat which were prepared in the same manner with OGTT test animal. On the day of the study, rats were orally dosed with the testing compounds (30 mg/kg) and 2 hr later, rats were dosed with insulin (0.25 U/kg, i.p.) in 0.1% BSA solution in saline. Blood glucose of the rat was measured at 15, 30, 60, 120 min after dose.

TABLE 5

AUC for glucose levels during ITT treated with compounds of Examples 1 and 2

| Compound | AUC of Glucose in high fat rat Observed value (mg/dl × 120 min) | % reduction |
|---|---|---|
| Control | 13359 | — |
| Example 1 | 11014 | 27.7 ($p < 0.02$) |
| Example 2 | 12796 | 4.2 |

The compounds of Examples 1 and 2 were tested for the blood glucose lowering effect in STZ rat and it did not reduce blood glucose (data not shown) which further confirmed that compounds of Examples 1 and 2 act as an insulin sensitizer not as an insulin mimetic.

What is claimed is:

1. A compound having the Formula I:

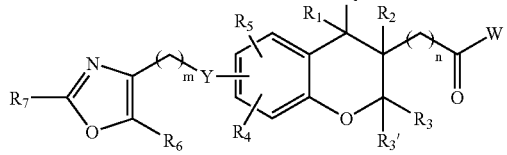

Formula I wherein $R_1$, $R_1'$, $R_2$, $R_3$ and $R_3'$ are independently selected from H, $C_{1-7}$ alkyl, $C_{2-7}$ alkenyl, $C_{2-7}$ alkynyl, and halogen, wherein alkyl, alkenyl and alkynyl are linear or branched and are optionally substituted with substituents selected from 1 to 7 halogen atoms and 1-3-$OC_{1-3}$ alkyl groups; $R_4$ and $R_5$ are independently selected from H, halogen, $C_{1-7}$ alkyl, $C_{2-7}$ alkenyl, $C_{2-7}$ alkynyl, —OH, and —$OC_{1-5}$ alkyl; $R_6$ and $R_7$ are independently selected from H, $C_{1-7}$ alkyl, $C_{2-7}$ alkenyl, $C_{2-7}$ alkynyl and an optionally substituted phenyl; Y is =O; W is selected from the group of consisting of —$OR_a$, —$NR_aR_b$, —$NR_aSO_2R_b$ wherein $R_a$ and $R_b$ are independently selected from the group consisting of H, $C_{1-4}$ alkyl and aryl where in all instances, alkyl is linear or branched and are optionally substituted with 1-7 halogen atoms; m and n are independently 0-6; and pharmaceutically acceptable salts thereof.

2. A compound having Formula 1 as recited in claim 1, wherein $R_1$, $R_1'$, $R_2$, $R_3$, $R_3'$, $R_4$ and $R_5$ are hydrogen.

3. A compound having the Formula 1 as recited in claim 1, wherein $R_6$ is selected from the group consisting of H, Me and Ph.

4. A compound having the Formula 1 as recited in claim 1, wherein $R_7$ is selected from the group consisting of H, Me, Et, Ph, optionally substituted with 1-3 halogens or phenyl.

5. A compound having the Formula 1 as recited in claim 1, wherein W is a group that is easily removed under physiological conditions during or after administration to a mammalian patient to yield a carboxylic acid selected from the group consisting of —$OR_a$, —$NR_aR_b$, wherein $R_a$ and $R_b$ are independently selected from Me and Et.

6. A compound as recited in claim 1, wherein the stereochemistry at the $C_3$ position of the chroman ring is R.

7. A compound as recited in claims 1, wherein the stereochemistry at the $C_3$ position of the chroman ring is S.

8. A compound as recited in claim 1, wherein the compound of the Formula I is selected from the following structures

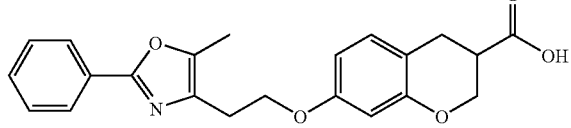

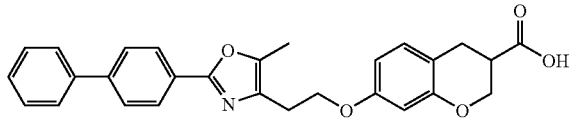

-continued

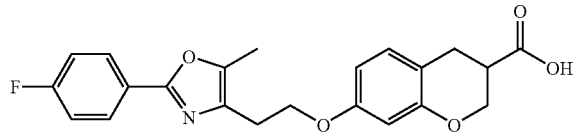

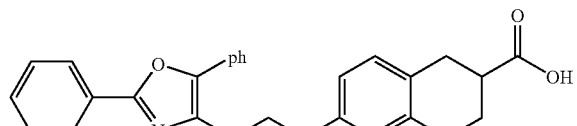

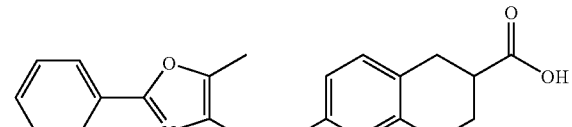

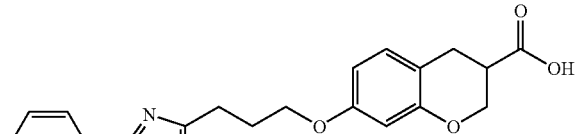

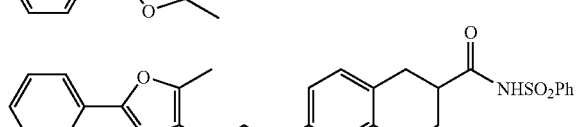

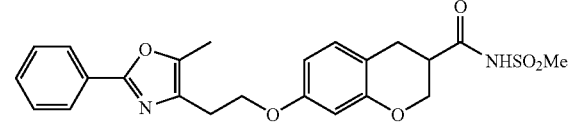

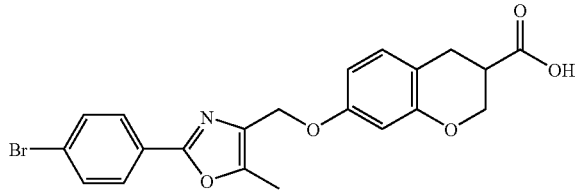

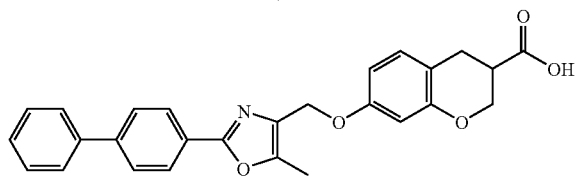

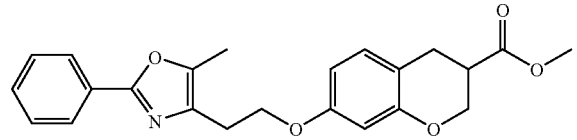

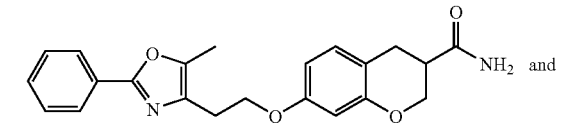 and

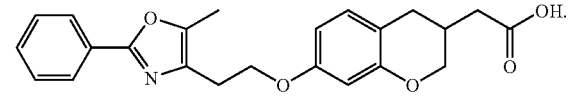

9. A compound as recited in claim 8, wherein the stereochemistry at the C₃ position of the chroman ring is R.

10. A compound as recited in claim 8, wherein the stereochemistry at the C₃ position of the chroman ring is S.

11. A compound as recited in claim 1, wherein $R_1$, $R_1'$, $R_2$, $R_3$, $R_3'$, $R_4$ and $R_5$ are all hydrogens, $R_6$ is methyl, $R_7$ is phenyl, m is 2, n is 0 and W is —OH and the C₃ position of the chroman ring is R, as shown below:

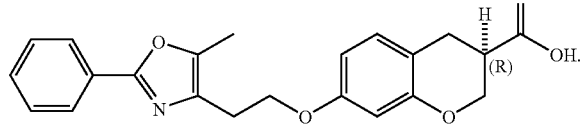

12. A compound as recited in claim 1, wherein $R_1$, $R_1'$, $R_2$, $R_3$, $R_3'$, $R_4$ and $R_5$ are all hydrogens, $R_6$ is methyl, $R_7$ is phenyl, m is 2, n is 0 and W is —OH and the C₃ position of the chroman ring is S, as shown below:

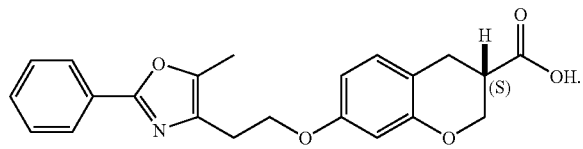

13. A compound as recited in claim 8, wherein said compound is in form of a pharmaceutically acceptable salt in which the carboxylic group exist as the anion and the counter cation is selected from Na, K, biguanide, arginine, lysine and histidine.

14. A pharmaceutical composition comprising an effective amount of compounds of Formula I of claim 1 and a pharmaceutically acceptable carrier.

15. A pharmaceutical composition comprising an effective amount of compounds of Formula I of claim 5 and a pharmaceutically acceptable carrier.

16. A method for treating or controlling non-insulin dependent (Type II) diabetes mellitus in a mammalian patient in need of such treatment which comprises administering to said patient a therapeutically effective amount of a compound of Formula I of claim 1.

17. A method for treating or controlling hyperglycaemia in a mammalian patient in need of such treatment which comprises administering to said patient a therapeutically effective amount of a compound of Formula I of claim 1.

18. A method of treating or controlling one or more diseases, disorders, or conditions selected form the group consisting of non-insulin dependent diabetes mellitus (NIDDM) and hyperglycemia comprising the administration of an effective amount of a compound of Formula I of claim 1.

19. The method in accordance with claim 18, additionally comprising the administration of an effective amount one or more of the compounds selected from the group consisting of:

(a) an insulin sensitizer selected from the group consisting of (i) biguanides including metformin and fenformin, (ii) PPARγ agonist including pioglitazone, rosiglitazone and englitazone, (iii) protein tyrosine phosphatase-1B (PTP-1B) inhibitors, and (iv) dipeptidyl peptidase IV inhibitors and (b) insulin.

* * * * *